(12) United States Patent
Tyler et al.

(10) Patent No.: US 9,802,818 B2
(45) Date of Patent: Oct. 31, 2017

(54) SORTING PROCESS OF NANOPARTICLES AND APPLICATIONS OF SAME

(75) Inventors: Timothy P. Tyler, Chicago, IL (US); Anne-Isabelle Henry, Chicago, IL (US); Richard P. Van Duyne, Wilmette, IL (US); Mark C. Hersam, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 709 days.

(21) Appl. No.: 13/461,521

(22) Filed: May 1, 2012

(65) Prior Publication Data

US 2012/0281213 A1     Nov. 8, 2012

Related U.S. Application Data

(60) Provisional application No. 61/481,994, filed on May 3, 2011.

(51) Int. Cl.
  *B82Y 30/00* (2011.01)
  *B82Y 40/00* (2011.01)
  *G01N 21/65* (2006.01)

(52) U.S. Cl.
  CPC ............. *B82Y 30/00* (2013.01); *B82Y 40/00* (2013.01); *G01N 21/658* (2013.01)

(58) Field of Classification Search
  CPC ...... B82Y 30/00; B82Y 40/00; G01N 21/658; G01N 21/65; G01N 21/63; G01N 21/00
  USPC ............. 436/45, 43; 977/773; 356/301, 300
  See application file for complete search history.

(56) References Cited

U.S. PATENT DOCUMENTS

| | | | |
|---|---|---|---|
| 2009/0140206 A1* | 6/2009 | Nie et al. | 252/301.16 |
| 2009/0149344 A1* | 6/2009 | Zhao et al. | 506/12 |
| 2009/0173918 A1* | 7/2009 | Hersam et al. | 252/502 |
| 2010/0072458 A1* | 3/2010 | Green et al. | 257/24 |

OTHER PUBLICATIONS

Tyler et al, Improved Monodispersity of Plasmonic Nanoantennas via Centrifugal Processing, The Journal of Physical Chemistry Letters, Jan. 18, 2011, 2, pp. 218-222.*
Arnold, Michael, et al., Hydrodynamic Characterization of Surfactant Encapsulated Carbon Nanotubes Using an Analytical Ultracentrifuge, ACS NANO, 2008, vol. 2, No. 11, pp. 2291-2300.*

(Continued)

*Primary Examiner* — Christine T Mui
(74) *Attorney, Agent, or Firm* — Locke Lord LLP; Tim Tingkang Xia, Esq.

(57) ABSTRACT

In one aspect of the present invention, a method for sorting nanoparticles includes preparing a high-viscosity density gradient medium filled in a container, dispersing nanoparticles into an aqueous solution to form a suspension of the nanoparticles, each nanoparticle having one or more cores and a shell encapsulating the one or more cores, layering the suspension of the nanoparticles on the top of the high-viscosity density gradient medium in the container, and centrifugating the layered suspension of the nanoparticles on the top of the high-viscosity density gradient medium in the container at a predetermined speed for a predetermined period of time to form a gradient of fractions of the nanoparticles along the container, where each fraction comprises nanoparticles in a respective one of aggregation states of the nanoparticles.

17 Claims, 10 Drawing Sheets

(56) References Cited

OTHER PUBLICATIONS

Wustholz, K. L. et al., Structure-Activity Relationships in Gold Nanoparticle Dimers and Trimers for Surface-Enhanced Raman Spectroscopy, J. Am. Chem. Soc., 2010, p. 10903-10910, vol. 132, No. 31.

Kneipp, K. et al., Single Molecule Detection Using Surface-Enhanced Raman Scattering (SERS), Phys. Rev. Lett., 1997, p. 1667-1670, vol. 78, No. 9.

Nie, S. M. et al., Probing Single Molecules and Single Nanoparticles by Surface-Enhanced Raman Scattering, Science, 1997, p. 1102-1106, vol. 275, No. 21.

Le Ru, E. C. et al., Proof of Single-Molecule Sensitivity in Surface Enhanced Raman Scattering (SERS) by Means of a Two-Analyte Technique, J. Phys. Chem. B, 2006, p. 1944-1948, vol. 110, No. 4.

Dieringer, J. A. et al., A Frequency Domain Existence Proof of Single-Molecule Surface-Enhanced Raman Spectroscopy, J. Am. Chem. Soc., 2007, p. 16249-16256, vol. 129, No. 51.

Michaels, A. M. et al., Ag Nanocrystal Junctions as the Site for Surface-Enhanced Raman Scattering of Single Rhodamine 6G Molecules, J. Phys. Chem. B, 2000, p. 11965-11971, vol. 104, No. 50.

Camden, J. P. et al., Probing the Structure of Single-Molecule Surface-Enhanced Raman Scattering Hot Spots. J. Am. Chem. Soc., 2008, p. 12616-12617, vol. 130, No. 38.

Moskovits, M. et al., Engineering Nanostructures for Giant Optical Fields, Chem. Phys. Lett., 2004, p. 91-95, vol. 397.

Rycenga, M. et al., Understanding the SERS Effects of Single Nanoparticles and Their Dimers, One at a Time, J. Phys. Chem. Lett., 2010, p. 696-703, vol. 1.

Stoerzinger, K. A. et al., Screening Nanopyramid Assemblies to Optimize Surface Enhanced Raman Scattering, J. Phys. Chem. Lett., 2010, p. 1046-1050, vol. 1.

Alvarez-Puebla, R. et al., Light Concentration at the Nanometer Scale, J. Phys. Chem. Lett., 2010, p. 2428-2434, vol. 1.

Jana, N. R. et al., Wet Chemical Synthesis of High Aspect Ratio Cylindrical Gold Nanorods, J. Phys. Chem. B, 2001, p. 4065-4067, vol. 105, No. 19.

Xia, Y. et al., Shape-Controlled Synthesis of Metal Nanocrystals: Simple Chemistry Meets Complex Physics?, Angew. Chem. Int. Ed., 2009, p. 60-103, vol. 48.

Wiley, B. et al., Shape-Controlled Synthesis of Metal Nanostructures: The Case of Silver, Chem. Eur. J., 2005, p. 454-463, vol. 11.

Liu, F.-K., Analysis and Applications of Nanoparticles in the Separation Sciences: A Case of Gold Nanoparticles, J. Chromatogr. A, 2009, p. 9034-9047, vol. 1216.

Hanauer, M. et al., Separation of Nanoparticles by Gel Electrophoresis According to Size and Shape, Nano Lett., 2007, p. 2881-2885, vol. 7, No. 9.

Surugau, N. et al., Electrophoretic Methods for Separation of Nanoparticles, J. Sep. Sci., 2009, p. 1889-1906, vol. 32.

Wei, G. T. et al., Shape Separation of Nanometer Gold Particles by Size-Exclusion Chromatography, Anal. Chem., 1999, p. 2085-2091, vol. 71, No. 11.

Liu, F.-K., SEC Characterization of Au Nanoparticles Prepared through Seed-Assisted Synthesis, Chromatographia, 2007, p. 791-796, vol. 66.

Sharma, V. et al., Shape Separation of Gold Nanorods Using Centrifugation, Proc. Natl. Acad. Sci., 2009, p. 4981-4985, vol. 106, No. 13.

Contado, C. et al., Size Sorting of Citrate Reduced Gold Nanoparticles by Sedimentation Field-Flow Fractionation, J. of Chromatogr. A, 2009, p. 9088-9098, vol. 1216.

Braun, G. B. et al., Generalized Approach to SERS-Active Nanomaterials via Controlled Nanoparticle Linking, Polymer Encapsulation, and Small-Molecule Infusion, J. Phys. Chem. C, 2009, p. 13622-13629, vol. 113, No. 31.

Sun, X. et al., Separation of Nanoparticles in a Density Gradient: FeCo@C and Gold Nanocrystals, Angew. Chem. Int. Ed., 2009, p. 939-942, vol. 48.

Bai, Lu. et al., Rapid Separation and Purification of Nanoparticles in Organic Density Gradients, J. Am. Chem. Soc., 2010, p. 2333-2337, vol. 132, No. 7.

Chen, G. et al., High-Purity Separation of Gold Nanoparticle Dimers and Trimers, J. Am. Chem. Soc., 2009, p. 4218-4219, vol. 131, No. 12.

Doering, W. E. et al., SERS as a Foundation for Nanoscale, Optically Detected Biological Labels, Adv. Mater., 2007, p. 3100-3108, vol. 19.

Arnold, M. S. et al., Sorting Carbon Nanotubes by Electronic Structure Using Density Differentiation, Nature Nanotech., 2006, p. 60-65, vol. 1.

Hersam, M. C., Progress Towards Monodisperse Single-Walled Carbon Nanotubes, Nature Nanotech., 2008, p. 387-394, vol. 3.

Green, A. A. et al., Solution Phase Production of Graphene with Controlled Thickness via Density Differentiation, Nano Lett., 2009, p. 4031-4036, vol. 9, No. 12.

Green, A. A. et al., Emerging Methods for Producing Monodisperse Graphene Dispersions, J. Phys. Chem. Lett., 2010, p. 544-549, vol. 1.

Green, A. A. et al., Processing and Properties of Highly Enriched Double-Wall Carbon Nanotubes, Nature Nanotech., 2009, p. 64-70, vol. 4.

Liu, L. et al., Recent Developments in Carbon Nanotube Sorting and Selective Growth, MRS Bulletin, 2010, p. 315-321, vol. 35.

Norman, T. J. et al., Near Infrared Optical Absorption of Gold Nanoparticle Aggregates, J. Phys. Chem. B, 2002, p. 7005-7012, vol. 106, No. 28.

Perrin, F., Brownian motion of an ellipsoid (II). Free rotation and depolarization of fluorescence. Translation and dissemination of ellipsoidal molecules, Mouvement Brownien d'un Ellipsoide (II). Rotation Libre et Dépolarisation des Fluorescences. Translation et Diffusion de Molécules Ellipsoidales. J. Phys. Radium, 1936, p. 1-11, vol. 7.

Eivindvik, K. et al., Physicochemical Properties of Iodixanol, Acta Radiologica, 1995, p. 32-38, vol. 36 (Suppl. 399).

* cited by examiner

SORTING PROCESS OF NANOPARTICLES AND APPLICATIONS OF SAME

CROSS-REFERENCE TO RELATED PATENT APPLICATIONS

This application claims priority to and the benefit of, pursuant to 35 U.S.C. §119(e), U.S. provisional patent application Ser. No. 61/481,994, filed May 3, 2011, entitled "IMPROVED MONODISPERSITY OF CORE/SHELL NANOPARTICLES VIA CENTRIFUGAL PROCESSING", by Timothy P. Tyler et al., the disclosure of which is incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [27] represents the 27-th reference cited in the reference list, namely, Arnold, M. S.; Green, A. A.; Hulvat, J. F.; Stupp, S. I.; Hersam, M. C. Sorting Carbon Nanotubes by Electronic Structure Using Density Differentiation. *Nature Nanotech.* 2006, 1, 60-65.

STATEMENT OF FEDERALLY-SPONSORED RESEARCH

This invention was made with government support under FA9550-08-1-0221 awarded by the Air Force Office of Scientific Research, DE-SC0001059 awarded by the Department of Energy, and CHE0911145, DMR0520513, and DMR1006391 awarded by the National Science Foundation. The government has certain rights in the invention.

FIELD OF THE INVENTION

The present invention relates generally to nanoparticles, and more particularly to centrifugal sorting processes of core/shell nanoparticles and applications of the same.

BACKGROUND OF THE INVENTION

The intense electromagnetic field arising at the surface of metallic nanostructures from the excitation of the localized surface plasmon resonance (LSPR) allows for the enhancement of the Raman intensity of adsorbed molecules by a factor up to $4 \times 10^8$ or greater [1]. The structures supporting this plasmonic phenomenon, known as surface-enhanced Raman scattering (SERS), are diverse. The most sensitive examples, with an enhancement factor large enough to observe spectra at the single molecule level [2-5], are aggregated metallic nanoparticles. Correlative structure-activity studies have indeed shown that the presence of a nanometer-sized junction [6, 7] or crevice [1, 8] creates the electromagnetic 'hot-spot' (i.e., 'nanoantenna') required to observe single molecule SERS. Recent investigations of the hot-spots at the junction of silver cubes [9] and gold pyramidal shells [10] or at the interface between a gold nanostar and a gold surface [11] have highlighted how the control over the structure of this nanometer-scale region is crucial for achieving high enhancement factors. While the early fundamental studies of single molecule SERS have been performed on inhomogeneous samples, the integration of plasmonic nanoantennas into reliable technological applications, such as high sensitivity biological and chemical sensors, requires improved structural reproducibility.

Homogeneous nanostructure populations can be realized via precisely controlled fabrication or post-synthetic sorting techniques. Although much effort has been devoted to the controlled synthesis of nanoparticles, structural polydispersity remains an issue [11-14]. Consequently, post-fabrication separation methods have become important for characterizing or refining populations of nanoparticles based on their size, shape, and aggregation state [15] For example, electrophoretic methods [16], most notably gel electrophoresis [17], have been used to separate metal nanoparticles by both size and shape. Size-exclusion chromatography has also been demonstrated for separating gold nanoparticles by shape [18] and as a tool for characterizing synthesized nanoparticles [19]. In addition, sedimentation coefficient differences between nanoparticles of varying size and shape have been exploited for sorting by centrifugation [20] and sedimentation field-flow fractionation [21]. In particular, a recent study on polymer-coated nanoparticle clusters employed centrifugation and filtration to remove single-core nanoparticles and large aggregates respectively, ultimately yielding samples of primarily multi-core nanoparticle clusters with enhanced SERS signals [22]. Finally, density gradient centrifugation has proven to be particularly successful for obtaining refined populations of nanoparticles, leading to narrow diameter and shape distributions [23, 24] or a specific aggregation state for nanoparticle clusters [25].

For plasmonic applications, the removal of single nanoparticles from aggregates is particularly desirable given that only nanoparticle aggregates (i.e., two or more metallic nanoparticles) have thus far been shown to provide sufficient enhancement for single molecule and single particle SERS [6]. Improved monodispersity within nanoantenna samples allows for increased ensemble SERS signals and removal of inactive species for potential sensing applications. Efforts toward improved monodispersity through controlled synthesis of nanoparticles have been unable to fully address this issue. Previous centrifugal sorting methods for nanoparticles have been limited to slower-sedimenting small diameter nanoparticles and have required chemical functionalization or surfactants to keep the nanoparticles dispersed in solution.

Therefore, a heretofore unaddressed need exists in the art to address the aforementioned deficiencies and inadequacies.

SUMMARY OF THE INVENTION

The present invention discloses, among other things, an aqueous surfactant-free centrifugal sorting method for plasmonic nanoantennas including silica-coated gold nanoparticle clusters that yields populations of predominantly one aggregation state and an enhanced ensemble SERS response. By using a high-viscosity medium, such as iodixanol, one is able to sort the relatively massive gold/silica nanoantennas by sedimentation coefficient via transient density gradient centrifugation, thus producing samples with a preponderance of a selected aggregation state. Furthermore, the silica shell allows the nanoparticles to be dispersed in water without further functionalization or surfactants, and also protects the SERS reporter molecules at the gold/silica interface. SERS ensemble measurements confirm an increased signal from fractions with a diminished monomer population that, when combined with improved control over nanoparticle cluster size, provides a route to improved reliability and reproducibility in plasmonic applications such as SERS-based sensors. This sorting approach can be applied to a wide variety of core/shell nanoparticle structures in general to achieve more monodisperse samples for relatively large nanoparticles.

In one aspect of the invention, a method for sorting nanoparticles comprises preparing an aqueous iodixanol density gradient medium filled in at least one centrifugal tube; dispersing nanoparticles into an aqueous solution to form a suspension of the nanoparticles, wherein each nanoparticle comprises one or more gold cores and a silica shell encapsulating the one or more gold cores; layering the suspension of the nanoparticles on the top of the aqueous iodixanol density gradient medium in the at least one centrifugal tube; centrifugating the layered suspension of the nanoparticles at a predetermined speed for a predetermined period of time to form a gradient of fractions of the nanoparticles in the at least one centrifugal tube, wherein each fraction comprises nanoparticles in a respective one of aggregation states of the nanoparticles; wherein each aggregation state is a monomer state or a cluster state that ranges from dimers to dodecamers; and collecting each fraction of the nanoparticles from the at least one centrifugal tube.

Each of the one or more gold cores has a size/diameter in a range of about 10 nm to about 500 nm. The silica shell has a thickness in a range of about 10 nm to about 150 nm.

In one embodiment, each nanoparticle further comprises SERS reporter molecules hosted at the interface of the gold core and the silica shell, where the SERS reporter molecules comprises (1,2-bis(4-pyridyl)ethylene (BPE)).

In one embodiment, the aqueous iodixanol density gradient medium comprises about 30%-60% weight per volume iodixanol.

In another aspect of the invention, a method for sorting nanoparticles includes preparing a high-viscosity density gradient medium filled in a container; dispersing nanoparticles into an aqueous solution to form a suspension of the nanoparticles, wherein each nanoparticle comprises one or more cores and a shell encapsulating the one or more cores; layering the suspension of the nanoparticles on the top of the high-viscosity density gradient medium in the container; and centrifugating the layered suspension of the nanoparticles on the top of the high-viscosity density gradient medium in the container at a predetermined speed for a predetermined period of time to form a gradient of fractions of the nanoparticles along the container, wherein each fraction comprises nanoparticles in a respective one of aggregation states of the nanoparticles.

Additionally, the method further includes collecting each fraction of the nanoparticles from the container.

In one embodiment, each of the one or more cores is formed of a noble metal, such as gold. In one embodiment, the shell is formed of a material such that the nanoparticles are dispersed in the aqueous solution without need for functionalization or surfactants. For example, the shell is formed of silicon.

In one embodiment, each nanoparticle further comprises SERS reporter molecules hosted at the interface of the core and the shell, where the SERS reporter molecules comprises (1,2-bis(4-pyridyl)ethylene (BPE)).

In one embodiment, each of the one or more cores has a size/diameter in a range of about 10 nm to about 500 nm, and wherein the shell has a thickness in a range of about 10 nm to about 150 nm. The nanoparticles are biocompatible.

In one embodiment, each of the aggregation states is corresponding to a monomer state or a cluster state that ranges from dimers to dodecamers.

In one embodiment, the high-viscosity density gradient medium comprises an aqueous iodixanol density gradient medium, wherein the aqueous iodixanol density gradient medium comprises about 30%-60% weight per volume iodixanol.

In one embodiment, the container comprises one or more centrifugal tubes.

In yet another aspect of the invention, a sensing platform comprises a substrate; an array of wells formed in the substrate; and sorted nanoparticles filling in the array of wells such that each well contains a single sorted nanoparticle, wherein the sorted nanoparticles are in a cluster state. The cluster state corresponds to one of a dimer state to a dodecamer state. The sorted nanoparticles are biocompatible.

In one embodiment, each sorted nanoparticle comprises two or more cores and a shell encapsulating the two or more cores. Each of the two or more cores is formed of a noble metal, such as gold. The shell is formed of a material such that the nanoparticles are dispersed in the aqueous solution without need for functionalization or surfactants. In one embodiment, the shell is formed of silicon.

In one embodiment, each sorted nanoparticle further comprises SERS reporter molecules hosted at the interface of the two or more cores and the shell, wherein the SERS reporter molecules comprises (1,2-bis(4-pyridyl)ethylene (BPE)).

In a further aspect of the invention, a microfluidic device comprises the sensing platform disclosed above.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
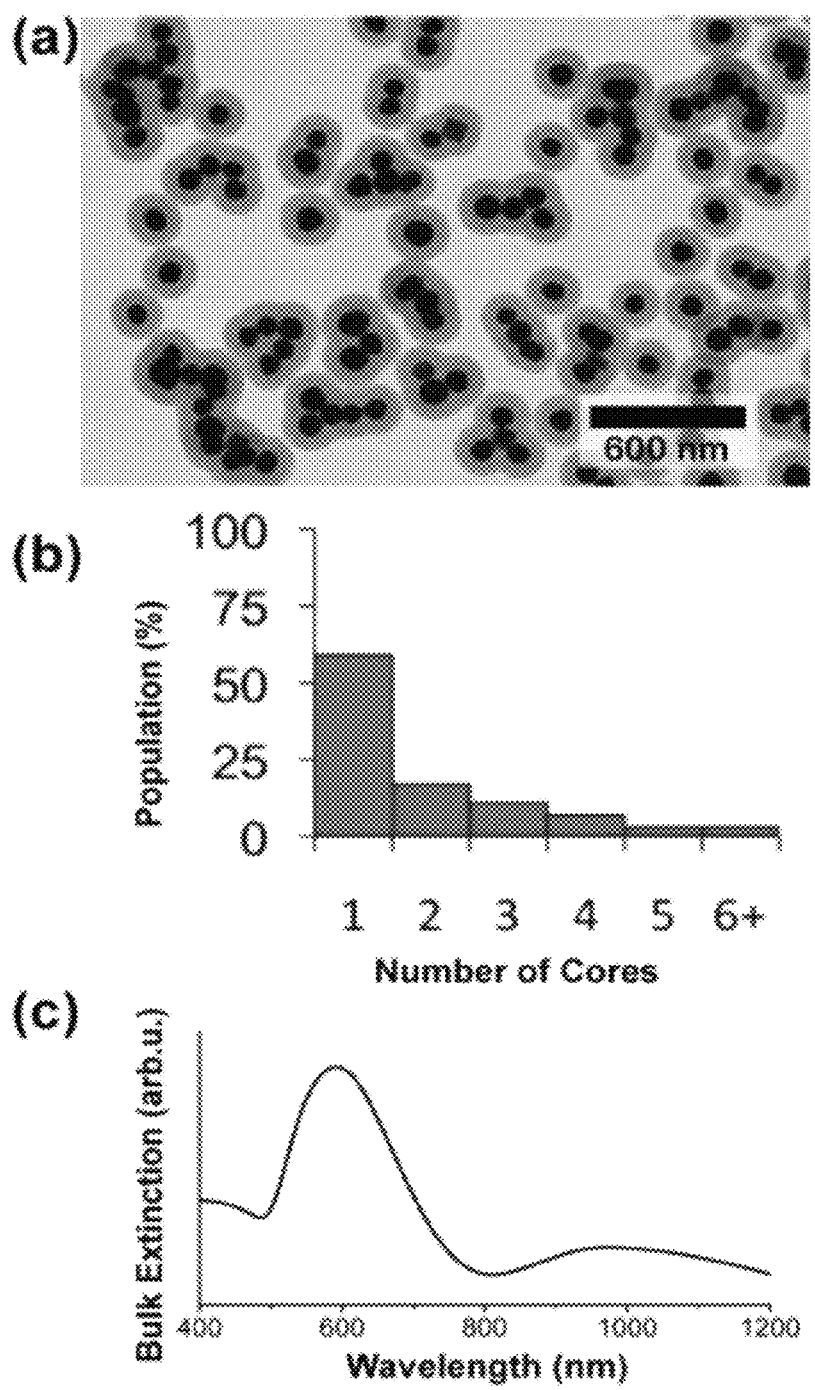
FIG. 1 shows characterization of the as-synthesized gold core/silica shell nanoparticle sample: (a) a representative TEM image showing the structure and variation in the number of gold cores within each silica shell, (b) a histogram of the populations as a function of the number of cores, and (c) an extinction spectrum of the as-synthesized sample dispersed in water.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. Additionally, titles or subtitles may be used in the specification for the convenience of a reader, which shall have no influence on the scope of the present invention.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, if any, the term "transmission electron microscopy" or its abbreviation "TEM" refers to a microscopy technique whereby a beam of electrons is transmitted through an ultra thin specimen, interacting with the specimen as it passes through. An image is formed from the interaction of the electrons transmitted through the specimen; the image is magnified and focused onto an imaging device, such as a fluorescent screen, on a layer of photographic film, or to be detected by a sensor such as a CCD camera.

As used herein, the term "surface enhanced Raman spectroscopy" or its abbreviation "SERS" refers to a surface-sensitive technique that enhances Raman scattering by molecules adsorbed on rough metal surfaces. The enhancement factor can be as much as $10^{10}$ to $10^{11}$, which means the technique may detect single molecules.

As used herein, if any, the term "scanning electron microscope" or its abbreviation "SEM" refers to a type of electron microscope that images the sample surface by scanning it with a high-energy beam of electrons in a raster scan pattern.

The electrons interact with the atoms that make up the sample producing signals that contain information about the sample's surface topography, composition and other properties such as electrical conductivity.

As used herein, "nanoscopic-scale", "nanoscopic", "nanometer-scale", "nanoscale", "nanocomposites", "nanoparticles", the "nano-" prefix, and the like generally refers to elements or objects of intermediate size between molecular and microscopic (micrometer-sized) structures, having widths or diameters of less than about 1 μm, preferably less than about 100 nm in some cases. In all embodiments, specified widths can be smallest width (i.e. a width as specified where, at that location, the article can have a larger width in a different dimension), or largest width (i.e. where, at that location, the object's width is no wider than as specified, but can have a length that is greater).

As used herein, the terms "comprising", "including", "carrying", "having", "containing", "involving", and the like are to be understood to be open-ended, i.e., to mean including but not limited to.

OVERVIEW OF THE INVENTION

Noble metal nanoparticle clusters underlie a variety of plasmonic devices and measurements including surface-enhanced Raman spectroscopy (SERS). Due to the strong dependence of plasmonic properties on nanoparticle cluster aggregation states, the elimination of non-SERS-active structures and the refinement of the nanoparticle cluster population are critical to realizing uniform and reproducible structures for plasmonic nanoantenna applications such as SERS-based sensors. SERS nanoantennas including aggregated spherical gold cores encapsulated in a protective silica shell with Raman reporter molecules adsorbed at the gold/silica interface have been shown to be ideal SERS substrates [1, 26], offering robustness and stability. The silica shell has the added benefit that it directly enables dispersion in aqueous solutions, thereby eliminating the need for additional chemical functionalization. While equilibrium isopycnic density gradient centrifugation techniques that are common for carbon-based nanomaterials [27-32] are incompatible with high-density structures such as nanoparticle clusters, sorting can, in principle, be accomplished by sedimentation coefficient in the transient centrifugal regime. However, in this study, the relatively large size of the gold cores (about 100 nm in diameter) combined with the silica shell (about 60 nm thick) makes sorting by transient motion challenging since these high-mass structures will sediment significantly faster than smaller nanoparticles. According to the invention, the issue is overcome by using the high-viscosity density gradient medium iodixanol, which slows the sedimentation of the gold/silica nanoparticle clusters to the point where structurally distinct fractions can be collected following centrifugation.

In one aspect, the invention relates to a centrifugal sorting technique for gold core/silica shell nanoparticles that host SERS reporter molecules at the gold/silica interface. In one embodiment, relatively massive nanoparticle clusters are sorted by sedimentation coefficient via centrifugation in a high-viscosity density gradient medium, such as an aqueous iodixanol density gradient medium, which yields solutions that contain a preponderance of one aggregation state and a diminished monomer population as determined by transmission electron microscopy (TEM), extinction spectroscopy, and SERS. A quantitative analysis of the nanoparticle sedimentation coefficients is presented, thus allowing this approach to be predictably generalized to other nanoparticle systems. According to the invention, the collected fractions are found to possess a preponderance of one aggregation state and a diminished monomer population, thus yielding ideal SERS nanoantennas that can be directly employed in a variety of plasmonic applications. In addition, the nanoparticle sedimentation coefficients are quantitatively analyzed, which facilitate the applications of this approach to other nanoparticle systems.

Accordingly, the sorting method includes preparing a high-viscosity density gradient medium filled in a container including, for example, one or more centrifugal tubes. In one embodiment, the high-viscosity density gradient medium is formed of about 30%-60% weight per volume iodixanol. Other composites can also be utilized to practice the invention.

The sorting method also includes dispersing nanoparticles to be sorted into an aqueous solution to form a suspension of the nanoparticles. The nanoparticles exist in a variety of aggregation states, which corresponds to monomers or clusters that ranges from dimers to dodecamers. Accordingly, each nanoparticle comprises one or more cores and a shell encapsulating the one or more cores. In one embodiment, each of the one or more cores is formed of a noble metal, such as gold. The shell is formed of a material such that the nanoparticles are dispersed in the aqueous solution without need for functionalization or surfactants. For example, the shell is formed of silicon. Each of the one or more cores has a size/diameter in a range of about 10 nm to about 500 nm. The shell has a thickness in a range of about 10 nm to about 150 nm. Additionally, each nanoparticle further comprises SERS reporter molecules hosted at the interface of the core and the shell, where the SERS reporter molecules comprises (1,2-bis(4-pyridyl)ethylene (BPE)).

Then, the suspension of the nanoparticles is carefully layered on the top of the high-viscosity density gradient medium in the container. Subsequently, the layered suspension of the nanoparticles on the top of the high-viscosity density gradient medium in the container is centrifuged at a predetermined speed for a predetermined period of time to form a gradient of fractions/bands of the nanoparticles along the container. Each fraction/band comprises nanoparticles in a respective one of aggregation states of the nanoparticles. Each fraction sorted nanoparticles are collected from the container for use.

Accordingly the invention, the silica coating keeps the nanoantennas dispersed in aqueous solutions without functionalization or surfactants, which avoids complications in their use in potential technological applications. The use of an aqueous iodixanol density gradient provides a sufficiently high solvent viscosity to compensate for their increased mass, allowing sorting by aggregation state to occur. The particularly low centrifugal forces required (about 500 g) and short times (about 10 min.) underscore the potential scalability of this process.

Figure 7:
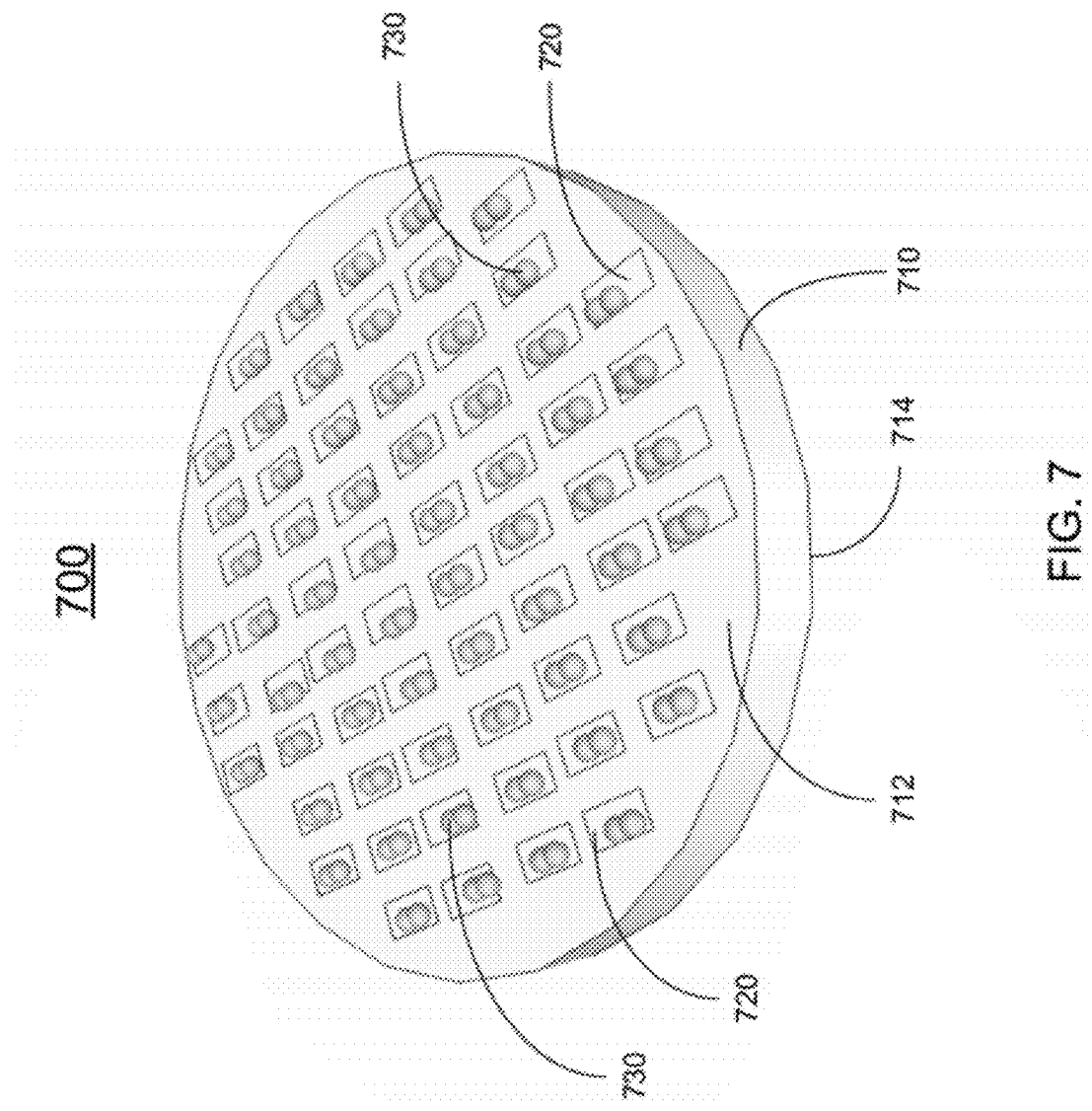
FIG. 7 shows schematic of sorted nanoantennas filling a welled sensing substrate according to one embodiment of the invention.

In another aspect, the invention relates to a sensing platform that utilizes the sorted nanoparticles as nanoantennas to sense. In one embodiment, as shown in FIG. 7, the sensing platform 700 has a substrate 710, an array of wells 720 formed in the substrate 710, and sorted nanoparticles 730 filling in the array of wells 720. The sorted nanoparticles are in a cluster state. The cluster state corresponds to one of a dimer state to a dodecamer state. In the exemplary embodiment, the majority of the sorted nanoparticles 730 filled in the array of wells 720 is in a dimer state. Additionally, each well 720 contains a single sorted nanoparticle 730. The sorted nanoparticles 730 are biocompatible.

As disclosed above, each sorted nanoparticle 730 may have two or more cores and a shell encapsulating the two or more cores. Each of the two or more cores is formed of a noble metal, such as gold. The shell is formed of a material such that the nanoparticles are dispersed in the aqueous solution without need for functionalization or surfactants. In one embodiment, the shell is formed of silicon. Each sorted nanoparticle may further comprises SERS reporter molecules hosted at the interface of the two or more cores and the shell, wherein the SERS reporter molecules comprises (1,2-bis(4-pyridyl)ethylene (BPE)).

In a further aspect of the invention, a microfluidic device comprises the sensing platform disclosed above.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1

Sorting of Nanoparticles Via Certrifugal Processing

In this example, sample nanoparticles to be sorted and the sorted nanoparticles were characterized by scanning TEM (STEM), UV-vis-NIR spectroscopy measurements and SERS ensemble measurements. Other characterization methods can also be used to practice the invention.

Electron microscopy characterization was performed on a Hitachi HD2300 scanning transmission electron microscope (STEM), operating in high-resolution TE mode at 200 kV. Prior to observation, the sample was prepared by drop-casting the solution of interest onto a TEM grid (300 mesh formvar/carbon type B grid, Ted Pella, Inc.) and allowed to dry in air.

UV-vis-NIR spectroscopy measurements were carried out on a Cary 5000 spectrophotometer (Varian, Inc.) operating in two-beam mode, where a reference sample (aqueous iodixanol solution) was illuminated and measured concurrently with the sample, and the absorbance of the reference was subtracted from the sample measurement. A baseline correction was also used to account for variation in optical paths between the beams. Spectra were obtained with a resolution of 1 nm and an integration time of 1.33 seconds.

SERS ensemble measurements were performed on 200-400 µL aqueous suspensions of nanoantennas. All SER spectra were collected on a custom-built macro setup. The 632.8 nm excitation was obtained using a HeNe laser (12 mW output power, 6 mW at the sample) (Research Electro-Optics). The SERS measurements employ 1 in. interference and notch filters (Semrock, Rochester, N.Y.), a single grating monochromator with the entrance slit set to 100 µm (Acton Research Corporation, Acton, Mass.), a liquid $N_2$ cooled charge-coupled device (CCD) detector (model Spec 10:400B, Roper Scientific, Trenton, N.J.), and a data acquisition system (Photometrics, Tucson, Ariz.). The spectral positions of the CCD pixels were calibrated using cyclohexane.

In this example, the sample nanoparticles to be sorted are as-synthesized gold core/silica shell nanoparticles (Cabot Security Materials, Inc.) having the SERS reporter molecules (1,2-bis(4-pyridyl)ethylene (BPE)) adsorbed at the gold/silica interface and exist in a variety of aggregation states.

A representative TEM image of the sample (HitachiHD2300 STEM operating at 200 kV in TE mode) is shown in FIG. 1($a$), where the nanoparticles are found to exist as monomers or clusters that range from dimers to dodecamers with approximately spherical gold cores (about 96±11 nm in diameter) encapsulated in a silica shell (about 63±4 nm). Monomers represent more than half (about 59%) of the sample population, as shown in the population histogram in FIG. 1($b$). The minority species include dimers (about 17%), trimers (about 11%), tetramers (about 7%), and pentamers (about 3%), with the remaining clusters possessing more than five cores. The bulk extinction spectrum of the nanoantennas suspended in water, as shown in FIG. 1($c$) contains one peak centered at about 600 nm and a broader band centered at about 950 nm. Monomers of the size used here have a single plasmon resonance band and contribute strongly to the extinction at about 600 nm. Single particle LSPR (localized surface plasmon resonance) measurements have shown that dimers and trimers have two plasmon resonance bands [1]. The shorter wavelength band varies in position from about 650 nm to about 850 nm depending on every structural detail, but is particularly sensitive to the interparticle gap distance in the sub-2 nm range. Similarly, the width of the resonance depends sensitively on the structural details. The longer wavelength band varies in position from about 800 nm to about 1000 nm and is also structure sensitive. Consequently, dimer, trimers, and probably tetramers contribute to the extinction in the tail of the ensemble band at about 600 nm as well as to the blue leading edge of the about 950 nm band. Multi-core clusters contribute the rest of the extinction for the about 950 nm band. While the multi-core clusters have demonstrated excellent SERS enhancement in previous correlated structure-SERS activity measurements performed on similar nanoparticles differing only by their reporter molecule [1], no surface-enhanced Raman (SER) signal is measured from monomers at low excitation power.

In this example, aqueous density gradients were formed using Optiprep 60% w/v iodixanol, 1.32 g cm$^{-3}$ (Axis-Shield, PLC). Gradients were formed in centrifuge tubes using a linear gradient maker (SG 15 Linear Gradient Maker, Hoefer, Inc.) with about 5 mL starting solutions of about 30% and about 60% w/v iodixanol. About 200 µL, of bath sonicated gold nanoparticle solution (0% iodixanol) was then carefully layered on the top of the gradient using a syringe and 23 gauge needle.

Centrifugal sorting of the as-synthesized gold core/silica shell nanoparticles was accomplished using a Beckman SW41Ti swinging bucket rotor. The centrifuge tubes were initially loaded with a linear density gradient of about 30%-60% weight per volume iodixanol (about 1.16-1.32 g cm$^3$). Then, about 200 µL, of an aqueous suspension of the as-synthesized gold core/silica shell nanoparticles were carefully layered on the top. Importantly, the silica coating allows the nanoparticles to be well dispersed in water without the need for additional chemical functionalization or surfactants. After centrifuging at a relatively low speed (with a low centrifugal force of about 500 g) for about 10 minutes, a well-defined band and subsequent gradient of material is observed, as shown in FIG. 2(a).

Figure 2:
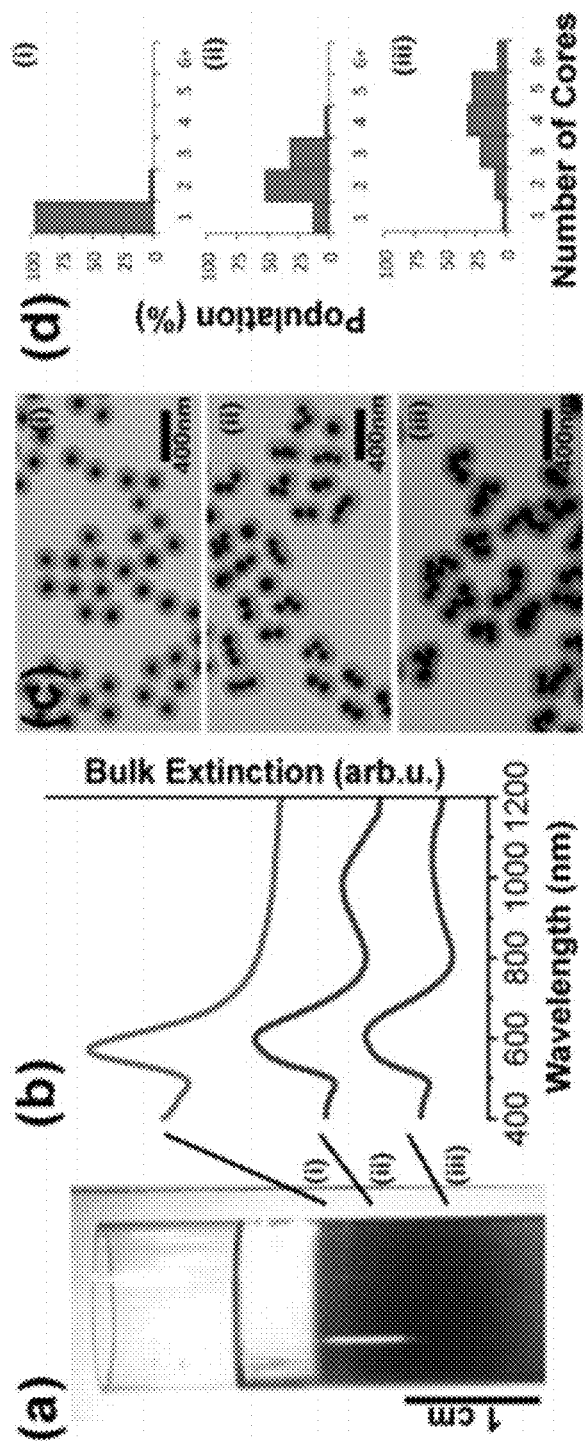
FIG. 2 shows (a) a photograph of a centrifuge tube after centrifugation of the sample in a surfactant-free aqueous iodixanol linear density gradient, (b) extinction spectra of three selected fractions, (i), (ii), and (iii), whose positions in the centrifugation tube are spatially indicated, (c) corresponding TEM images of the selected fractions, and (d) corresponding population histograms of the selected fractions.

Millimeter fractions were collected from the tube for TEM characterization using a piston gradient fractionator (Biocomp Instruments, Inc., Canada), and the resulting extinction spectra and aggregation state histograms based on particle counting from the TEM images for three of the fractions, labeled (i), (ii), and (iii), are shown in FIG. 2. The extinction spectra were measured by UV-vis-NIR spectroscopy in solution for the collected fractions and are shown in FIG. 2(b). In the top band (i), only the surface plasmon band near 570 nm is present. On the other hand, for fractions at lower positions in the centrifuge tube, a new broad band in the near-IR known to correspond to multi-core aggregates [33] is apparent, and the surface plasmon band is broadened and red-shifted. These spectra thus provide evidence that sorting by nanoparticle aggregation state has occurred with the top band likely enriched in monomers and subsequent bands possessing nanoparticle clusters. Analysis of the TEM images, as shown in FIG. 2(c), and its histograms, as shown in FIG. 2(d), verifies this assignment by directly showing that the top band (i) contains almost exclusively monomers (about 97%), while subsequent fractions possess an increasing quantity and size of nanoparticle clusters. In particular, fraction (ii) includes dimers (about 52%), trimers (about 32%), and monomers (about 13%), while fraction (iii) includes tetramers (about 32%), pentamers (about 28%), trimers (about 21%), dimers (about 9%), and monomers (about 3%). Even though monomers are found outside the top band, at a sufficient tube depth, they are reduced to a negligible proportion of the population, thus implying fractions that consist almost exclusively of SERS-active nano-antennas.

Figure 3:
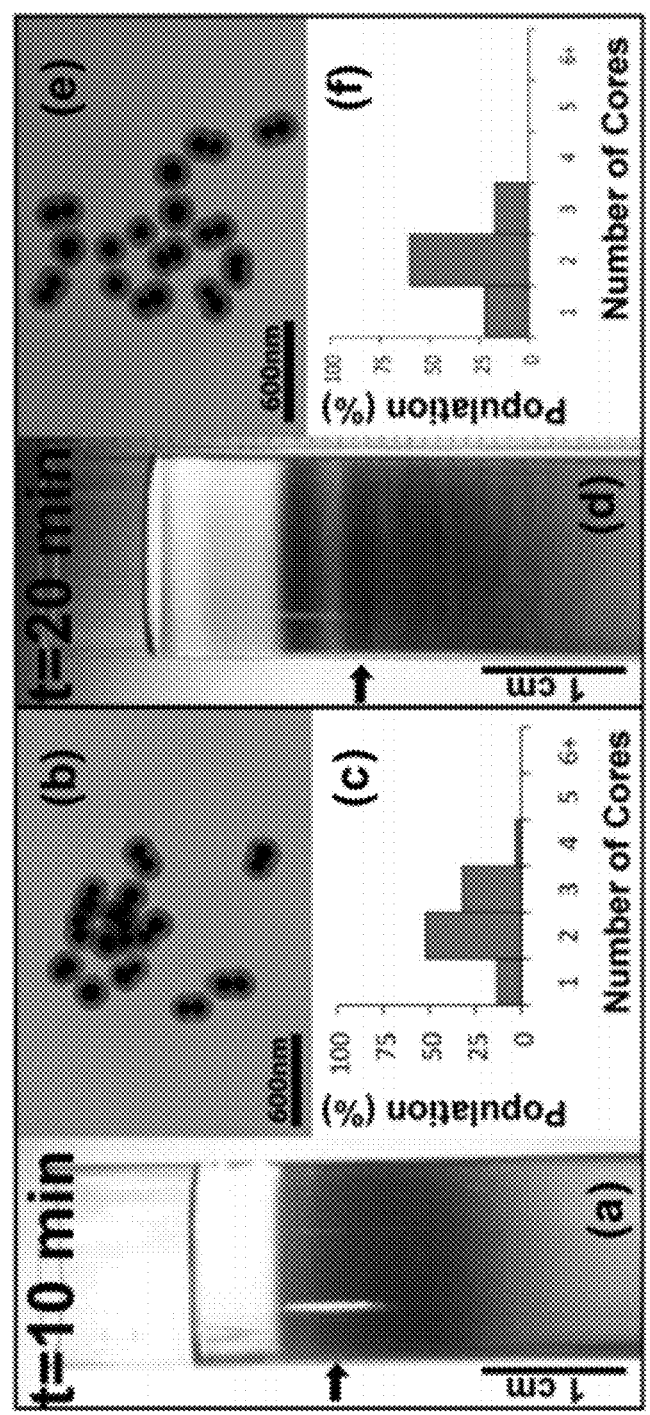
FIG. 3 shows centrifuge tube images (a) and (d) of separations running at 10 minutes and 20 minutes, respectively. Corresponding fractions are spatially indicated, each accompanied by a sample TEM image (b)/(e) and histogram (c)/(f) of aggregation states. A modest improvement in sorting is observed, although the concentration of dimers remains under 75%.

While the sorting method is highly effective at both removing monomers and targeting a narrow range of aggregation states, fractions other than the top band contain more than one nanoparticle aggregation state. To determine if this remaining polydispersity resulted from insufficient spatial separation of the bands in the centrifuge tube and/or imprecise fractionation, the centrifugation time was increased to spread the sorted material over a larger length of the centrifuge tube. Sorting experiments were carried out using the same sample and gradient preparation as described above for the original separation. Centrifugation time was doubled from about 10 minutes to about 20 minutes to allow bands of sorted material to spread further down the centrifuge tube, as shown in FIG. 3, where centrifuge tube images (a) and (d) of separations are for the centrifugation times of about 10 minutes and about 20 minutes, respectively. Corresponding fractions are spatially indicated, each accompanied by a sample TEM image (b)/(e) and histogram (c)/(f) of aggregation states. A modest improvement in sorting is observed, although the concentration of dimers remains under 75%.

Since the experiment provided minimal refinement compared to the original separation, the nanoclusters of differing aggregation states likely possess overlapping sedimentation coefficients. For example, the variability in the gold core diameter and shell thickness yields a distribution of nanoparticle cluster mass and volume. The effect of the structural polydispersity on the sedimentation coefficient distribution is exacerbated at higher nanoparticle aggregation states where multiple gold cores compound the variability in the nanoparticle cluster mass and volume. Furthermore, nanoparticle clusters including multiple gold cores can adopt a range of geometries (i.e., aspect ratios), which also influences the sedimentation coefficient.

Figure 4:
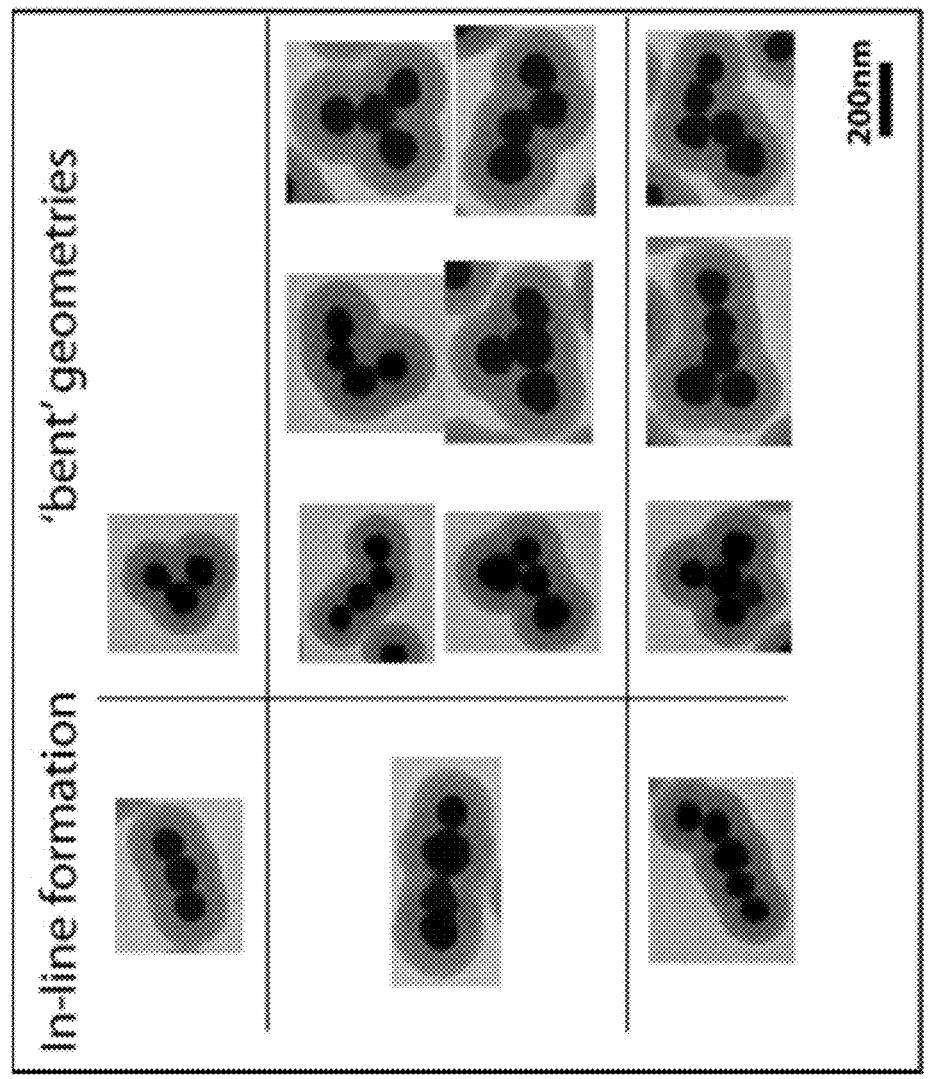
FIG. 4 shows aggregates assembled in a line, or in a random non-linear orientation. For this analysis, all aggregates were approximated as prolate ellipsoids with an appropriate aspect ratio derived from the TEM data.

To quantify the polydispersity in sedimentation coefficient as a function of nanoparticle aggregation state, a large number of nanoparticles (greater than 600) from the as-synthesized sample were imaged in TEM. The core diameters and aspect ratios were then individually extracted from the TEM data. The sedimentation coefficient can then be calculated using the following equation:

$$s = \frac{m(1 - \rho_s/\rho_p)}{f},$$

where m is the total particle mass, $\rho_s$ and $\rho_p$ are the densities of the solvent and particle respectively, and f is the frictional coefficient, which depends on the shape of the nanoparticle and the viscosity of the solvent. Aggregates larger than dimers possess a variety of shapes, requiring a thorough analysis to account for varying aspect ratios. To account for the observed variation in shape, as shown in FIG. 4, the nanoparticles were modeled as prolate ellipsoids using the total volume of gold obtained from the core diameters, the average silica shell thickness, and the individually measured aspect ratios. In one embodiment, the aspect ratios were measured for each individual aggregate and included in the final sedimentation coefficient analysis.

The frictional coefficient was then calculated using the Perrin equation for frictional ratios of ellipsoids of revolution [34], which modifies the frictional coefficient of a sphere with a geometrical correction factor P as follows:

$$f_{ellipsoid} = P(3\pi\eta d),$$

where $P = (1-q^2)^{1/2}/[q^{2/3}(\ln(\{1+(1-q^2)^{1/2}\}/q))]$

Here, $\eta$ is the viscosity of the solvent, d is the effective diameter of the equivalent sphere, and q is the aspect ratio of the prolate ellipsoid where q<1.

Figure 5:
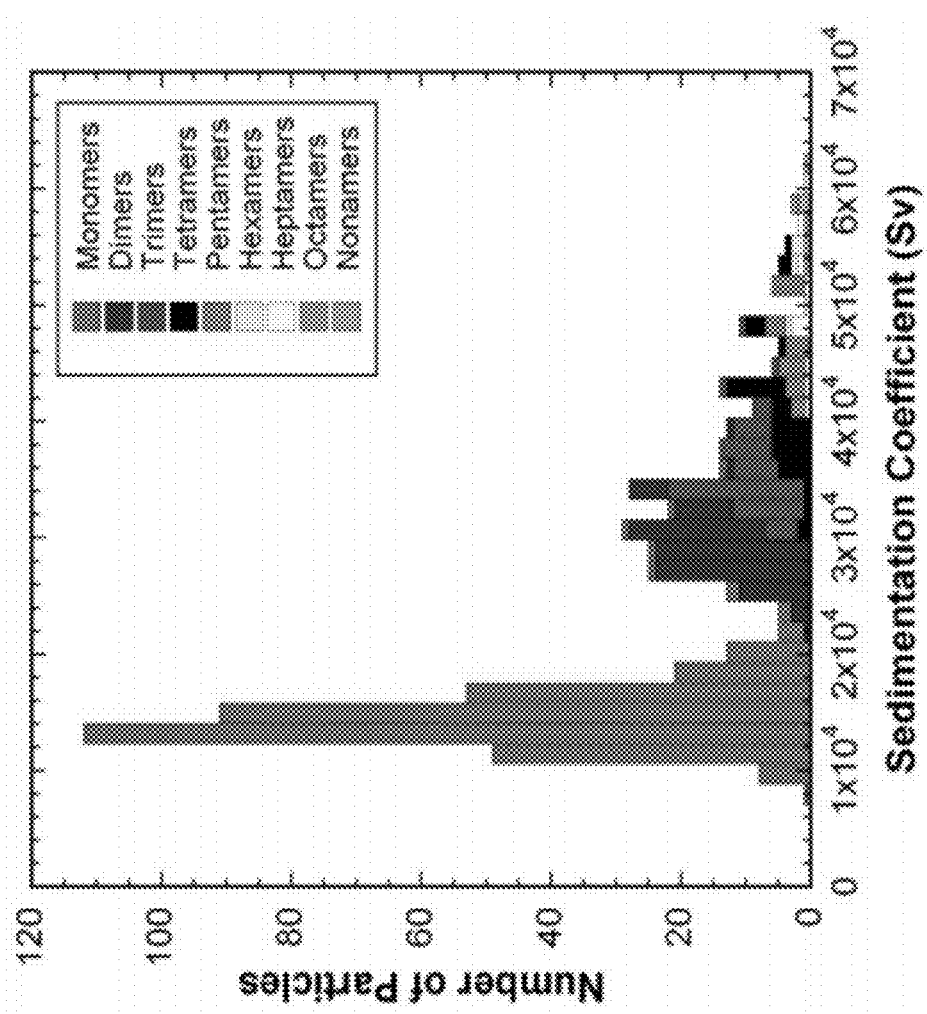
FIG. 5 shows a histogram of sedimentation coefficients for varying aggregation states, calculated by applying a Perrin ellipsoid model to individually measured nanoclusters. This model predicts high purity separation of monomers, followed by overlapping domains of dimers, trimers, tetramers, and higher order clusters, in agreement with the experimental data.

Using this ellipsoidal model and the structural parameters extracted from TEM, the distribution of sedimentation coefficients was calculated for the as-synthesized sample at a fixed point (about 40% w/v iodixanol, about 1.21 g cm$^{-3}$) in the density gradient [35], as shown in FIG. 5. This model reveals the presence of a monomer band at low sedimentation coefficients, followed by a gap in sedimentation coefficient, and finally overlapping aggregation states at higher sedimentation coefficients. Consequently, transient centrifugal sorting is expected to yield highly enriched monomers at the top of the centrifuge tube and then increasing but overlapping levels of nanoparticle aggregation for subsequent fractions, in agreement with the experimental results. This model thus holds promise for evaluating the feasibility and/or refining the experimental conditions for sorting other nanoparticle clusters via transient density gradient centrifugation techniques, assuming that the initial nanoparticle structural parameters and polydispersity have been determined. On the other hand, the results of transient density gradient centrifugation experiments can provide quantitative insight into the structural polydispersity of nanoparticle samples.

Figure 6:
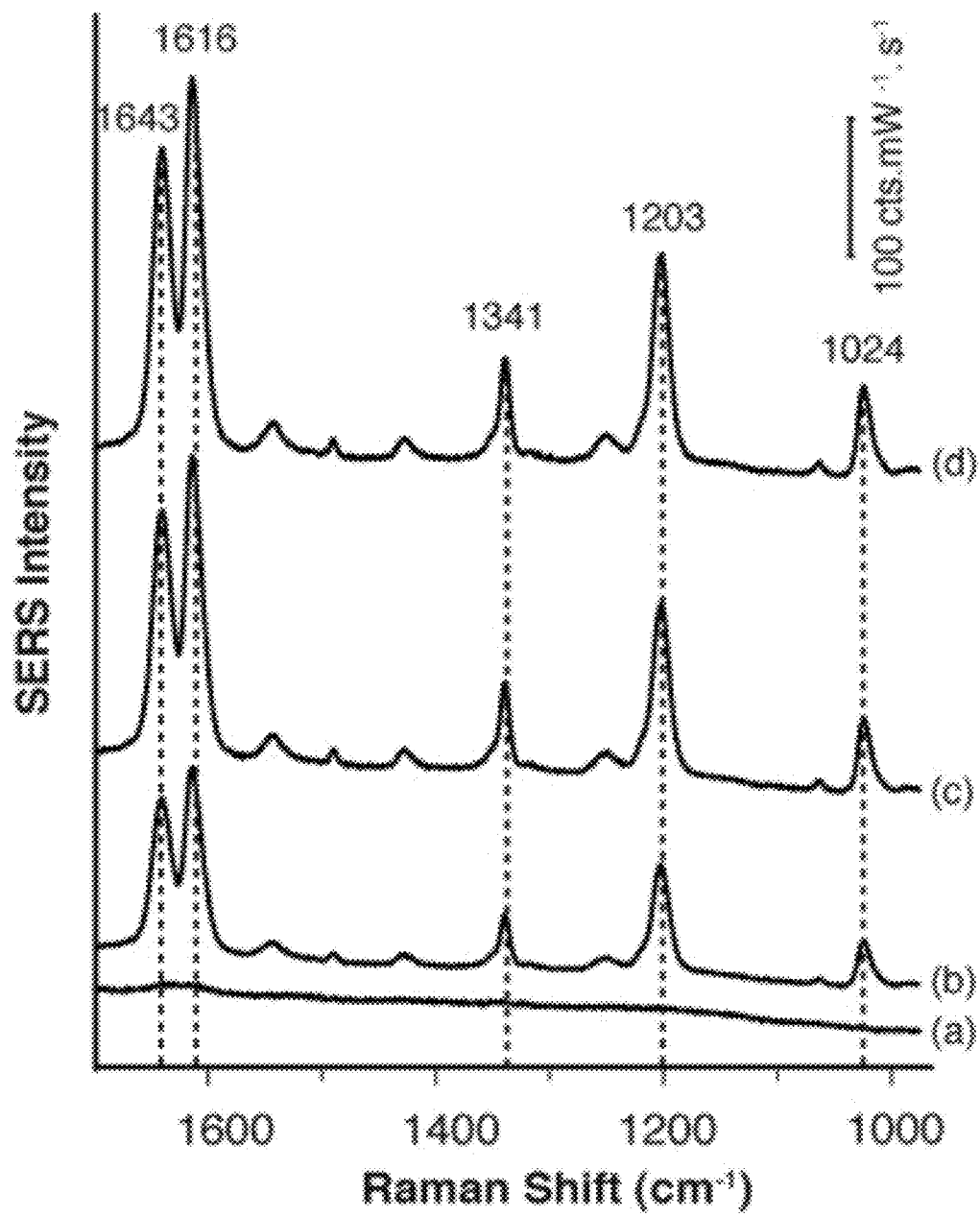
FIG. 6 shows measured SER spectra of 1,2-bis(4-pyridyl) ethylene (BPE), from (a) fraction (i), (b) the initial solution, (c) fraction (ii) enriched in dimers, and (d) fraction (iii) enriched in tetramers when illuminated at a 632.8 nm excitation wavelength and power of 6.0 mW.

To show the utility of the sorted nanoparticle clusters, ensemble averaged SERS measurements were performed on the initial solution and the selected fractions (i), (ii), and (iii). The nanoparticle concentrations were balanced between the samples using the visible surface plasmon band in the extinction spectra. The SER spectra of 1,2-bis(4-pyridyl)ethylene (BPE) were collected using excitation at a wavelength of about 632.8 nm and power of about 6 mW (HeNe laser 17 mW from Research Electro-optics). The spectra were acquired for about 15 seconds with 3 accumulations. The fraction enriched in monomers (i) exhibited no peaks, i.e. no SER signal was observed (spectrum (a), FIG. 6), which is in agreement with results published earlier on similar SERS nanoantennas [1]. The initial solution (spectrum (b), FIG. 6), exhibited the characteristic peaks of BPE including 1616 $cm^{-1}$, 1643 $cm^{-1}$, 1203 $cm^{-1}$, 1341 $cm^{-1}$, and 1024 $cm^{-1}$ in decreasing intensity. The same peaks were observed with the same intensity ratio on the measured SER spectra from the fractions enriched in dimers and trimers (ii) (spectrum (c), FIG. 6) and tetramers (iii) (spectrum (d), FIG. 6). The intensities of the peaks from the sorted fractions, where the amount of monomers has been substantially reduced, are higher than for the initial solution. This increase in SER signal is further evidence that centrifugal sorting has yielded samples enriched in SERS-active nanoantennas.

Both the nanoparticle cluster sorting technique and the resulting refined populations of plasmonic nanoantennas can find a wide range of potential applications. This sorting mechanism can be applied to a vast array of nanoscale core/shell structures, allowing for improved population control over particles too massive for current centrifugal sorting techniques. There are currently numerous applications for nanoparticles, including drug delivery, industrial coatings, battery anodes, and solar cells, which could benefit from greater control over nanoparticle population and enable larger structures to be used without necessitating large variation in particle size and shape. Core/shell nanoparticles specifically have found applications in optical sensing, MRI, fluorescence imaging, pigments, and catalysis. Plasmonic nanoantennas in particular are currently being used in the security industry for unique tagging and sensing applications, and more monodisperse samples could yield higher detection signals and improved reliability and reproducibility between samples.

Example 2

Sensing Platform

In this exemplary embodiment, a sensing platform that utilizes the centrifugally sorted core/shell nanoantennas for detecting and eliminating blood-borne pathogens is shown. This work is focused toward creating a dialysis-like therapeutic system whereby blood cycles through a portable device, is continuously sensed, and pathogens are removed via manipulation and separation of the fluid. The sorted core/shell nanoantennas have demonstrated a dramatic improvement in sensing capabilities by amplifying a key parameter, a percentage of active sensing sites, and are now being incorporated into the design of this system.

The sensing component of the sensing platform device includes a substrate containing an array of wells, into which the nanoantennas are inserted via fluid deposition. The surface design and deposition have been optimized such that nearly every well is filled with a nanoantenna.

The sensing capabilities of the substrate come from the nanoantennas themselves, whose nature and surface coverage are critical for high-performance sensing. After the nanoantennas are deposited from solution onto the substrate, their performance is assessed by SERS and the contents of the wells are quantitatively evaluated via SEM. By sorting the initial nanoantenna population to maximize the deposited number of active nanoantennas (dimers, trimers, . . . ) and minimize the number of inactive species (monomers), the sensing capabilities of the resulting welled substrate can be increased.

Referring to FIG. 7, a sensing platform 700 is schematically shown according to one embodiment of the present invention. The sensing platform 700 includes a substrate 710 having a top surface 712 and an opposite, bottom surface 714, an array of wells 720 formed on the top surface 712 of the substrate 710, and sorted nanoantennas 730 filling in the array of wells 720. The sorted nanoantennas 730 can be in a cluster state as dimers, trimers, . . . , or dodecamers. In the exemplary embodiment shown in FIG. 7, the sorted nanoantennas 730 are in a dimer state.

After depositing centrifugally sorted core/shell nanoantennas 730 onto the wells 720 on the top surface 712 of the substrate 710, it was observed that the population of wells containing inactive nanoantennas decreased from about 72% to about 11% as compared to unsorted as-synthesized nanoparticales, and the population in the wells 720 containing high-performance dimer and trimer nanoantennas increased from about 26% to about 86%. This dramatic improvement is shown in FIGS. 8 and 9.

Figure 8:
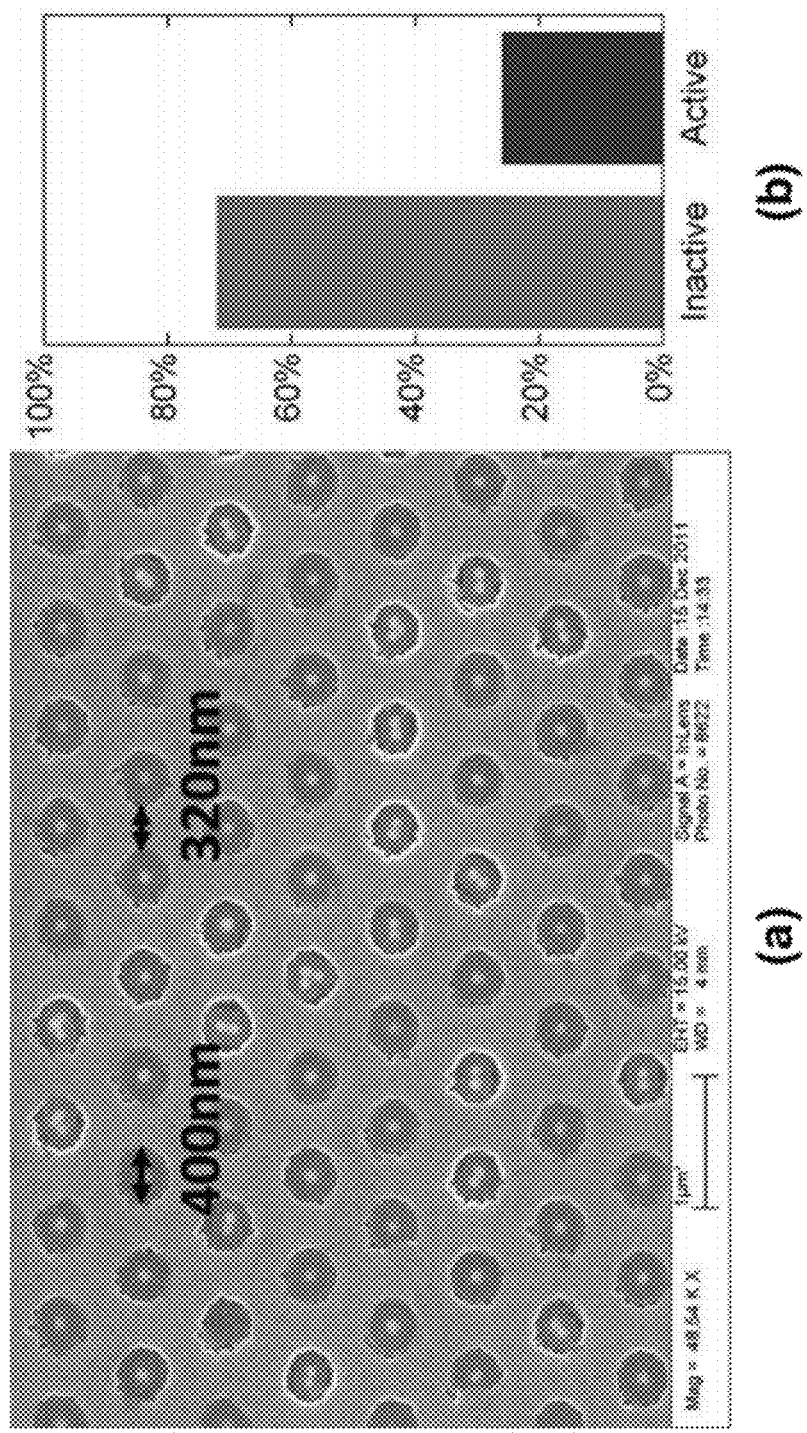
FIG. 8 shows an SEM image of a welled substrate containing unsorted nanoantennas, where the vast majority is monomers, i.e. inactive.

FIG. 8 shows an SEM image (a) of the array of wells containing unsorted nanoantennas of the sensing platform, and its corresponding histogram of the pollutions (b), where the vast majority of the populations in the array of wells is monomers, i.e., inactive.

Figure 9:
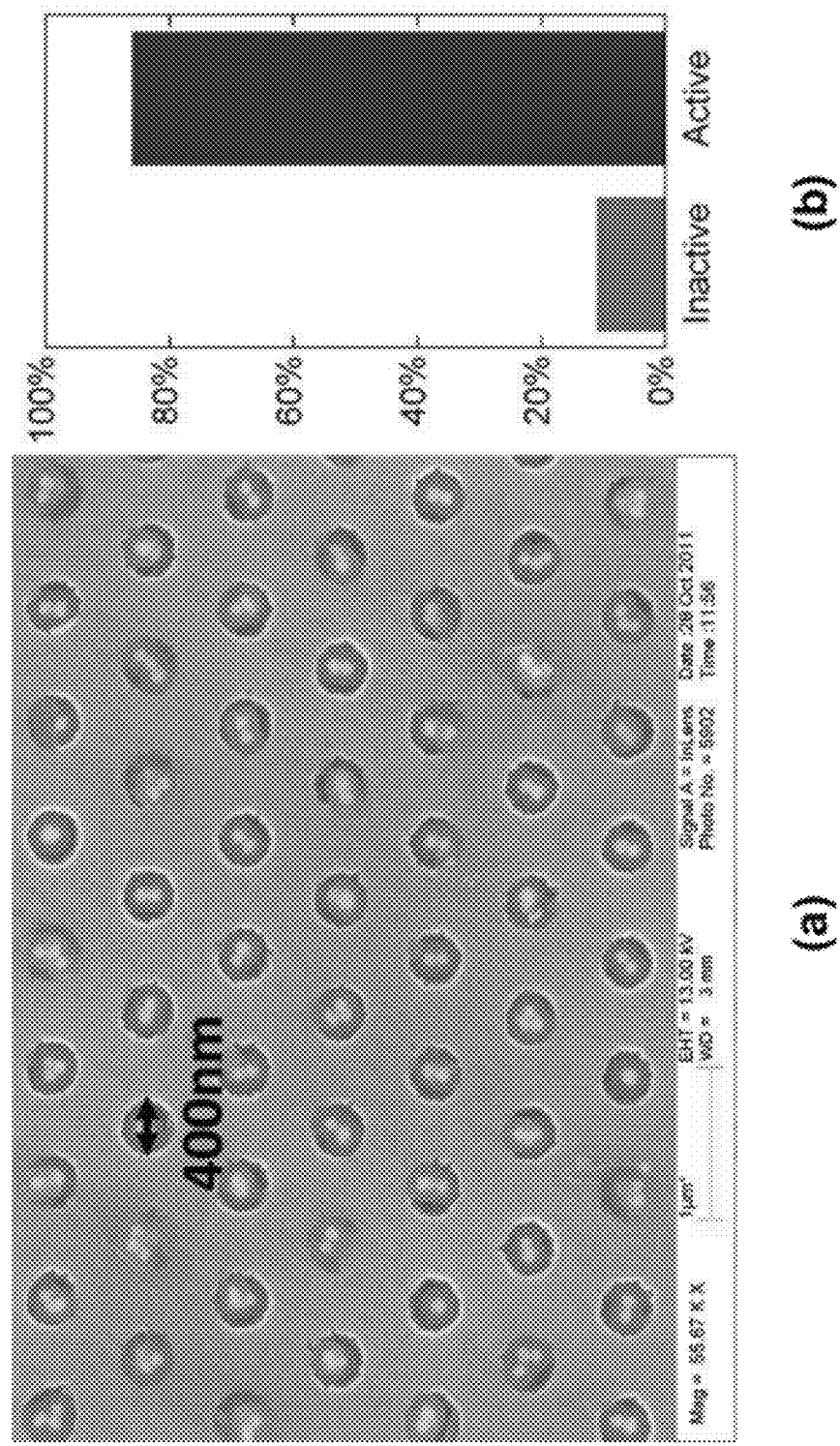
FIG. 9 shows an SEM image of a welled substrate containing centrifugally sorted nanoantennas according to one embodiment of the invention, where the population of inactive species (monomers) is minimal.

FIG. 9 shows an SEM image (a) of the array of wells containing the centrifugally sorted nanoantennas, and its corresponding histogram of the pollutions (b), where the vast majority of the populations in the array of wells is dimers, trimers, . . . , i.e., active, while the populations of inactive species (monomers) are minimal.

After optimizing the sensing capabilities of the sensing platform using the sorted nanoantennas, this architecture has been successfully integrated into a microfluidic device and SERS spectra have been obtained. This demonstrates that the nanoantenna-in-wells geometry combined with using the core/shell sorting method is both compatible with and enhances the capabilities of the microfluidic device.

Figure 10:
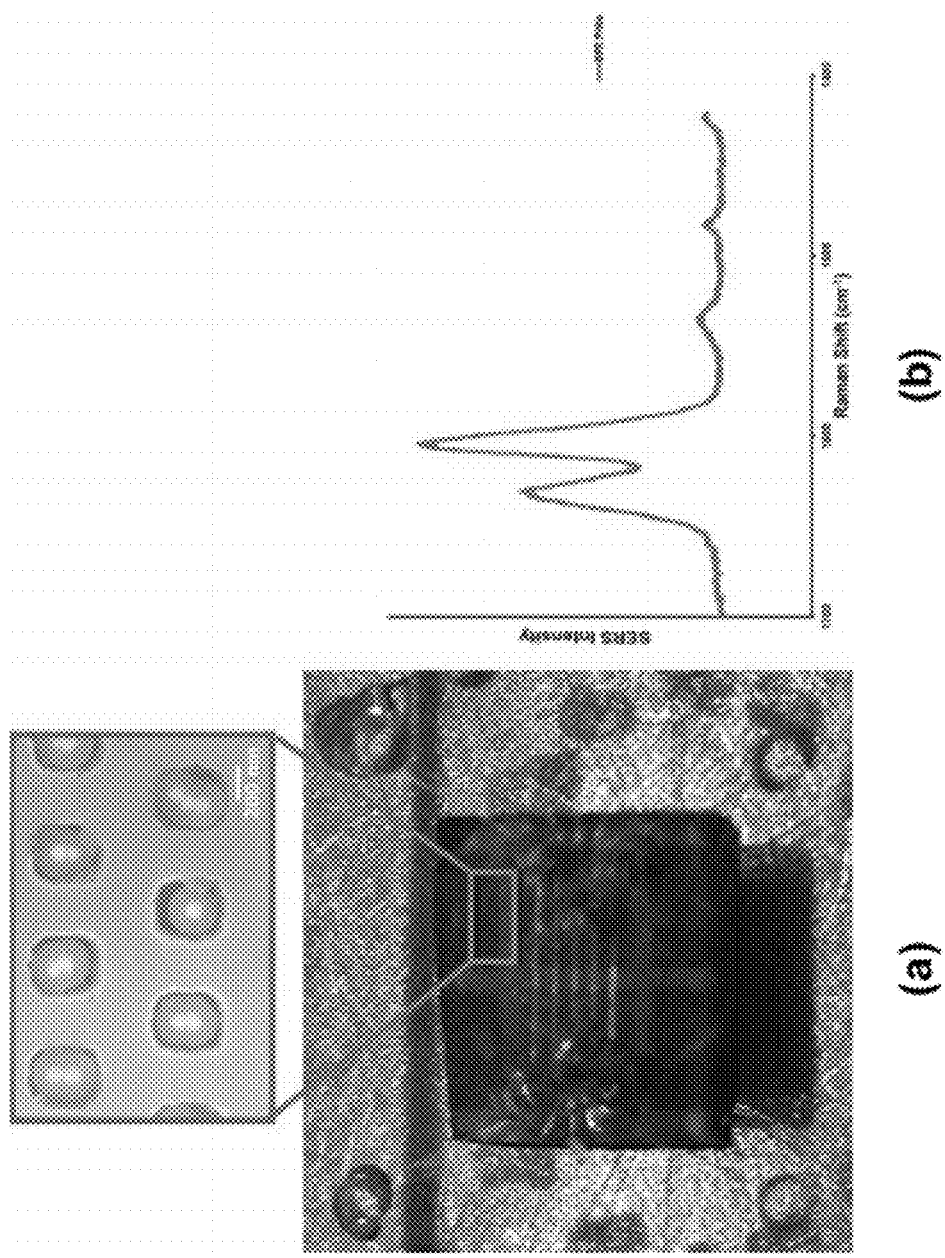
FIG. 10 shows an optical microscope image of a microfluidic device incorporating a nanoantenna-in-wells substrate (inset) according to one embodiment of the invention. Raman spectra have successfully been measured, demonstrating that this detection system is compatible with the microfluidic architecture.

FIG. 10 shows an optical microscope image (a) of such a microfluidic device incorporating a nanoantenna-in-wells substrate (inset). Raman spectra (b) have successfully been measured, demonstrating that this detection system is compatible with the microfluidic architecture.

In summary, the present invention, among other things, recites a facile, surfactant-free method for sorting high-mass silica-coated gold nanoparticle clusters by aggregation state via transient density gradient centrifugation. The improved monodispersity of the nanoparticle clusters is quantified by TEM, extinction spectroscopy, and SERS. Furthermore, a quantitative model is presented that accurately mirrors the observed sorting results and provides guidance to future efforts to separate other nanoparticles in the transient sedimentation regime. By removing non-SERS-active monomers and narrowing the nanoparticle aggregation state distribution, density gradient centrifugation serves as an effective post-synthetic processing technique for realizing uniform and reproducible structures for plasmonic nanoantenna applications such as SERS-based sensors.

Both the nanoparticle cluster sorting technique and the resulting refined populations of plasmonic nanoantennas can find a wide range of potential applications. This sorting mechanism can be applied to a vast array of nanoscale core/shell structures, allowing for improved population control over particles too massive for current centrifugal sorting techniques. The sorted nanoantennas can be utilized in sensing platform and microfluidic devices that are particularly effective at treating sepsis, a life-threatening condition where the bloodstream is overwhelmed with bacteria, wound infection, autoimmune diseases, cancer, diabetes, and regenerative medicine.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1] Wustholz, K. L.; Henry, A.-I.; McMahon, J. M.; Freeman, R. G.; Valley, N.; Piotti, M. E.; Natan, M. J.; Schatz, G. C.; Van Duyne, R. P. Structure-Activity Relationships in Gold Nanoparticle Dimers and Trimers for Surface-Enhanced Raman Spectroscopy. *J. Am. Chem. Soc.* 2010, 132, 10903-10910.

[2] Kneipp, K.; Wang, Y.; Kneipp, H.; Perelman, L. T.; Itzkan, I.; Dasari, R. R.; Feld, M. S. Single Molecule Detection Using Surface-Enhanced Raman Scattering (SERS). *Phys. Rev. Lett.* 1997, 78, 1667-1670.

[3] Nie, S. M.; Emory, S. R. Probing Single Molecules and Single Nanoparticles by Surface-Enhanced Raman Scattering. *Science* 1997, 275, 1102-1106.

[4] LeRu, E. C.; Meyer, M.; Etchegoin, P. G. Proof of Single-Molecule Sensitivity in Surface Enhanced Raman Scattering (SERS) by Means of a Two-Analyte Technique. *J. Phys. Chem. B* 2006, 110, 1944-1948.

[5] Dieringer, J. A.; Lettan, R. B. II; Scheidt, K. A.; Van Duyne, R. P. A Frequency Domain Existence Proof of Single-Molecule Surface-Enhanced Raman Spectroscopy. *J. Am. Chem. Soc.* 2007, 129, 16249-16256.

[6] Michaels, A. M.; Jiang, J.; Brus, L. Ag Nanocrystal Junctions as the Site for Surface-Enhanced Raman Scattering of Single Rhodamine 6G Molecules. *J. Phys. Chem. B* 2000, 104, 11965-11971.

[7] Camden, J. P.; Dieringer, J. A.; Wang, Y.; Masiello, D. J.; Marks, L. D.; Schatz, G. C.; Van Duyne, R. P. Probing the Structure of Single-Molecule Surface-Enhanced Raman Scattering Hot Spots. *J. Am. Chem. Soc.* 2008, 130, 12616-12617.

[8] Moskovits, M.; Jeong, D. H. Engineering Nanostructures for Giant Optical Fields. *Chem. Phys. Lett.* 2004, 397, 91-95.

[9] Rycenga, M.; Camargo, P. H. C.; Weiyang, L.; Moran, C. H.; Xia, Y. Understanding the SERS Effects of Single Nanoparticles and Their Dimers, One at a Time. *J. Phys. Chem. Lett.* 2010, 1, 696-703.

[10] Stoerzinger, K. A.; Hasan, W.; Lin, J. Y.; Robles, A.; Odom, T. W. Screening Nanopyramid Assemblies to Optimize Surface Enhanced Raman Scattering. *J. Phys. Chem. Lett.* 2010, 1, 1046-1050.

[11] Alvarez-Puebla, R.; Liz-Marzan, L. M.; Garcia de Abajo, F. J. Light Concentration at the Nanometer Scale. *J. Phys. Chem. Lett.* 2010, 1, 2428-2434.

[12] Jana, N. R.; Gearheart, L.; Murphy, C. J. Wet Chemical Synthesis of High Aspect Ratio Cylindrical Gold Nanorods. *J. Phys. Chem. B* 2001, 105, 4065-4067.

[13] Xia, Y.; Xiong, Y.; Lim, B.; Skrabalak, S. E. Shape-Controlled Synthesis of Metal Nanocrystals: Simple Chemistry Meets Complex Physics? *Angew. Chem. Int. Ed.* 2009, 48, 60-103.

[14] Wiley, B.; Sun, Y.; Mayers, B.; Xia, Y. Shape-Controlled Synthesis of Metal Nanostructures: The Case of Silver. *Chem. Eur. J.* 2005, 11, 454-463.

[15] Liu, F.-K. Analysis and Applications of Nanoparticles in the Separation Sciences: A Case of Gold Nanoparticles. *J. Chromatogr. A* 2009, 1216, 9034-9047.

[16] Hanauer, M.; Pierrat, S.; Zins, I.; Lotz, A.; Sonnichsen, C. Separation of Nanoparticles by Gel Electrophoresis According to Size and Shape. *Nano Lett.* 2007, 7, 2881-2885.

[17] Surugau, N.; Urban, P. L. Electrophoretic Methods for Separation of Nanoparticles. *J. Sep. Sci.* 2009, 32, 1889-1906.

[18] Wei, G. T.; Liu, F. K.; Wang, C. R. C. Shape Separation of Nanometer Gold Particles by Size-Exclusion Chromatography. *Anal. Chem.* 1999, 71, 2085-2091.

[19] Liu, F.-K. SEC Characterization of Au Nanoparticles Prepared through Seed-Assisted Synthesis. *Chromatographia* 2007, 66, 791-796.

[20] Sharma, V.; Park, K.; Srinivasarao, M. Shape Separation of Gold Nanorods Using Centrifugation. *Proc. Natl. Acad. Sci. USA* 2009, 106, 4981-4985.

[21] Contado, C.; Argazzi, R. Size Sorting of Citrate Reduced Gold Nanoparticles by Sedimentation Field-Flow Fractionation. *J. Chromatogr. A* 2009, 1216, 9088-9098.

[22] Braun, G. B.; Lee, S. J.; Laurence, T.; Fera, N.; Fabris, L.; Bazan, G. C.; Moskovits, M.; Reich, N. O. Generalized Approach to SERS-Active Nanomaterials via Controlled Nanoparticle Linking, Polymer Encapsulation, and Small-Molecule Infusion. *J. Phys. Chem. C* 2009, 113, 13622-13629.

[23] Sun, X.; Tabakman, S. M.; Seo, W.-S.; Zhang, L.; Zhang, G.; Sherlock, S.; Bai, L.; Dai, H. Separation of Nanoparticles in a Density Gradient: FeCo@C and Gold Nanocrystals. *Angew. Chem. Int. Ed.* 2009, 48, 939-942.

[24] Bai, Lu.; Ma, X.; Liu, J.; Sun, X.; Zhao, D.; Evans, D. E. Rapid Separation and Purification of Nanoparticles in Organic Density Gradients. *J. Am. Chem. Soc.* 2010, 132, 2333-2337.

[25] Chen, G.; Wang, Y.; Tan, L. H.; Yang, M.; Tan, L. S.; Chen, Y.; Chen, H. High-Purity Separation of Gold Nanoparticle Dimers and Trimers. *J. Am. Chem. Soc.* 2009, 131, 4218-4219.

[26] Doering, W. E.; Piotti, M. E.; Natan, M. J.; Freeman, R. G. SERS as a Foundation for Nanoscale, Optically Detected Biological Labels. *Adv. Mater.* 2007, 19, 3100-3108.

[27] Arnold, M. S.; Green, A. A.; Hulvat, J. F.; Stupp, S. I.; Hersam, M. C. Sorting Carbon Nanotubes by Electronic Structure Using Density Differentiation. *Nature Nanotech.* 2006, 1, 60-65.

[28] Hersam, M. C. Progress Towards Monodisperse Single-Walled Carbon Nanotubes. *Nature Nanotech.* 2008, 3, 387-394.

[29] Green, A. A.; Hersam, M. C. Solution Phase Production of Graphene with Controlled Thickness via Density Differentiation. *Nano Lett.* 2009, 9, 4031-4036.

[30] Green, A. A.; Hersam, M. C. Emerging Methods for Producing Monodisperse Graphene Solutions. *J. Phys. Chem. Lett.* 2010, 1, 544-549.

[31] Green, A. A.; Hersam, M. C. Processing and Properties of Highly Enriched Double-Wall Carbon Nanotubes. *Nature Nanotech.* 2009, 4, 64-70.

[32] Liu, L.; Hersam, M. C. Recent Developments in Carbon Nanotube Sorting and Selective Growth. *MRS Bulletin,* 2010, 35, 315-321.

[33] Norman, T. J., Jr.; Grant, C. D.; Magana, D.; Zhang, J. Z. Near Infrared Optical Absorption of Gold Nanoparticle Aggregates. *J. Phys. Chem. B,* 2002, 106, 7005-7012.

[34] Perrin, F. Mouvement Brownien d'un Ellipsoide (II). Rotation Libre et Depolarisation des Fluorescences. Translation et Diffusion de Molecules Ellipsoidales. *J. Phys. Radium,* 1936, 7, 1-11.

[35] Eivindvik, K.; Sjøgren, C. E. Physicochemical Properties of Iodixanol. *Acta Radiologica* 1995, 36 (Suppl. 399), 32-38.

What is claimed is:

1. A method for sorting nanoparticles, comprising:
   (a) preparing an aqueous iodixanol density gradient medium filled in at least one centrifugal tube, wherein the aqueous iodixanol density gradient medium is formed of about 30%-60% weight per volume iodixanol;
   (b) dispersing nanoparticles into an aqueous solution to form a suspension of the nanoparticles, wherein each nanoparticle comprises one or more gold cores and a silica shell encapsulating the one or more gold cores, wherein the shell is formed such that the nanoparticles are dispersed in the aqueous solution without need for functionalization or surfactants;
   (c) layering the suspension of the nanoparticles on the top of the aqueous iodixanol density gradient medium in the at least one centrifugal tube;
   (d) centrifuging the layered suspension of the nanoparticles at a predetermined speed with a centrifugal force of about 500 g for a predetermined period of time about 10 minutes to form a gradient of fractions of the nanoparticles in the at least one centrifugal tube by sedimentation coefficients of the nanoparticles in a transient centrifugal regime so as to sort the nanoparticles according to their sedimentation coefficients, wherein the sedimentation coefficient of a fraction of the nanoparticles satisfies with the relationship of:

$$s = \frac{m(1 - \rho_s/\rho_p)}{f},$$

where m is a total nanoparticle mass of the fraction, $\rho_s$ and $\rho_p$ are respectively densities of the aqueous iodixanol density gradient medium and the fraction of the nanoparticles, and f is a frictional coefficient that depends on a shape of the fraction of the nanoparticles and a viscosity of the aqueous iodixanol density gradient medium;

wherein each fraction comprises nanoparticles in a respective one of aggregation states of the nanoparticles;

wherein each aggregation state is a monomer state or a cluster state that ranges from dimers to dodecamers; and wherein the nanoparticles are separated in the at least one centrifugal tube according to their sedimentation coefficients so that a fraction of the nanoparticles in the monomer state is in a top portion of the at least one centrifugal tube and fractions of the nanoparticles in the cluster state that ranges from dimers to dodecamers are subsequently underneath the fraction of the nanoparticles in the monomer state in the at least one centrifugal tube; and (e) collecting each fraction of the nanoparticles from the at least one centrifugal tube.

2. The method of claim 1, wherein each nanoparticle further comprises Surface-Enhanced Raman Scattering (SERS reporter molecules hosted at the interface of the gold core and the silica shell.

3. The method of claim 2, wherein the SERS reporter molecules comprises (1,2-bis(4-pyridyl)ethylene (BPE)).

4. The method of claim 1, wherein each of the one or more gold cores has a size/diameter in a range of about 10 nm to about 500 nm, and wherein the silica shell has a thickness in a range of about 10 nm to about 150 nm.

5. A method for sorting nanoparticles, comprising:
   (a) preparing a high-viscosity density gradient medium filled in a container, wherein the aqueous iodixanol density gradient medium is formed of about 30%-60% weight per volume iodixanol;
   (b) dispersing nanoparticles into an aqueous solution to form a suspension of the nanoparticles, wherein each nanoparticle comprises one or more cores and a shell encapsulating the one or more cores, wherein the shell is formed of a material such that the nanoparticles are dispersed in the aqueous solution without need for functionalization or surfactants;
   (c) layering the suspension of the nanoparticles on the top of the high-viscosity density gradient medium in the container; and
   (d) centrifuging the layered suspension of the nanoparticles on the top of the high-viscosity density gradient medium in the container at a predetermined speed with a centrifugal force of about 500 g for a predetermined period of time about 10 minutes to form a gradient of fractions of the nanoparticles along the container by sedimentation coefficients of the nanoparticles in a transient centrifugal regime so as to sort the nanoparticles according to their sedimentation coefficients, wherein the sedimentation coefficient of a fraction of the nanoparticles satisfies with the relationship of:

$$s = \frac{m(1 - \rho_s/\rho_p)}{f},$$

where m is a total nanoparticle mass of the fraction, $\rho_s$ and $\rho_p$ are respectively densities of the high-viscosity density gradient medium and the fraction of the nanoparticles, and f is a frictional coefficient that depends on a shape of the fraction of the nanoparticles and a viscosity of the high-viscosity density gradient medium;

wherein each fraction comprises nanoparticles in a respective one of aggregation states of the nanoparticles;

wherein each aggregation state is a monomer state or a cluster state that ranges from dimers to dodecamers; and wherein the nanoparticles are separated in the container according to their sedimentation coefficients so that a fraction of the nanoparticles in the monomer state is in a top portion of the container and fractions of the nanoparticles in the cluster state that ranges from dimers to dodecamers are subsequently underneath the fraction of the nanoparticles in the monomer state in the container.

6. The method of claim 5, further comprising collecting each fraction of the nanoparticles from the container.

7. The method of claim 5, wherein each nanoparticle further comprises Surface-Enhanced Raman Scattering (SERS reporter molecules hosted at the interface of the core and the shell.

8. The method of claim 7, wherein the SERS reporter molecules comprises (1,2-bis(4-pyridyl)ethylene (BPE)).

9. The method of claim 5, wherein the nanoparticles are biocompatible.

10. The method of claim 5, wherein each of the aggregation states is corresponding to a monomer state or a cluster state that ranges from dimers to dodecamers.

11. The method of claim 5, wherein each of the one or more cores has a size/diameter in a range of about 10 nm to about 500 nm, and wherein the shell has a thickness in a range of about 10 nm to about 150 nm.

12. The method of claim 5, wherein each of the one or more cores is formed of a noble metal.

13. The method of claim 12, wherein each of the one or more cores is formed of gold.

14. The method of claim 5, wherein the shell is formed of a material such that the nanoparticles are dispersed in the aqueous solution without need for functionalization or surfactants.

15. The method of claim 14, wherein the shell is formed of silicon.

16. The method of claim 5, wherein the high-viscosity density gradient medium comprises an aqueous iodixanol density gradient medium.

17. The method of claim 5, wherein the container comprises one or more centrifugal tubes.

* * * * *